US008889243B2

(12) United States Patent
Hanschen et al.

(10) Patent No.: US 8,889,243 B2
(45) Date of Patent: *Nov. 18, 2014

(54) MECHANICAL FASTENING NETS AND METHODS OF MAKING THE SAME

(75) Inventors: Thomas P. Hanschen, Mendota Heights, MN (US); Ronald W. Ausen, St. Paul, MN (US); William C. Unruh, Inver Grove Heights, MN (US); William J. Kopecky, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/587,655

(22) Filed: Aug. 16, 2012

(65) Prior Publication Data

US 2014/0050883 A1 Feb. 20, 2014

(51) Int. Cl.
| | |
|---|---|
| B32B 3/26 | (2006.01) |
| B32B 3/30 | (2006.01) |
| B32B 7/04 | (2006.01) |
| B32B 7/12 | (2006.01) |
| B32B 37/04 | (2006.01) |
| A44B 18/00 | (2006.01) |
| B29C 70/14 | (2006.01) |
| B29C 59/04 | (2006.01) |
| B29C 47/00 | (2006.01) |
| B29D 28/00 | (2006.01) |
| A61F 13/512 | (2006.01) |
| A61F 13/15 | (2006.01) |

(52) U.S. Cl.
CPC ............ *A44B 18/0049* (2013.01); *B29D 28/00* (2013.01); *B29C 70/14* (2013.01); *B29C 59/04* (2013.01); *B32B 3/266* (2013.01); *B32B 3/30* (2013.01); *B32B 7/04* (2013.01); *A61F 13/512* (2013.01); *A61F 13/15731* (2013.01)

USPC ............ 428/131; 428/99; 428/100; 428/134; 428/137; 428/141; 264/310

(58) Field of Classification Search
None
See application file for complete search history.

(56) References Cited

U.S. PATENT DOCUMENTS 3,012,275 A 12/1961 Nalle, Jr.
3,252,181 A * 5/1966 Hureau ........................ 425/224
(Continued)

FOREIGN PATENT DOCUMENTS

DE 102006038334 2/2008
EP 0755665 1/1997
(Continued)

OTHER PUBLICATIONS

U.S. Application entitled, "Mechanical Fastener", filed Aug. 16, 2012, having U.S. Appl. No. 29/429,799.
(Continued)

*Primary Examiner* — Aaron Austin
*Assistant Examiner* — Donald M Flores, Jr.

(57) ABSTRACT

A method of making a mechanical fastening net. The method includes providing a net having strands of polymer and open areas between the strands of polymer and molding a portion of the polymer in the strands of the net into upstanding posts to form the mechanical fastening net. A mechanical fastening net that includes a polymeric backing, a plurality of openings in the polymeric backing, and upstanding posts on at least one of the first or second major surface of the polymeric backing is also disclosed. The polymeric backing has a range of thicknesses ranging from minimum to maximum thickness, and for at least a portion of the polymeric backing, the minimum thickness of the polymeric backing is where it abuts one of the openings.

20 Claims, 11 Drawing Sheets

(56) References Cited

U.S. PATENT DOCUMENTS

| | | | |
|---|---|---|---|
| 3,717,908 A | 2/1973 | Perina | |
| 3,831,741 A | 8/1974 | Poupitch | |
| 3,985,599 A | 10/1976 | Lepoutre | |
| 3,985,600 A | 10/1976 | Blais | |
| 4,001,366 A * | 1/1977 | Brumlik | 264/147 |
| 4,038,008 A | 7/1977 | Larsen | |
| 4,152,479 A * | 5/1979 | Larsen | 428/910 |
| 4,384,022 A | 5/1983 | Fowler | |
| 4,634,485 A | 1/1987 | Welygan | |
| 4,636,419 A | 1/1987 | Madsen | |
| 4,661,389 A | 4/1987 | Mudge | |
| 4,775,310 A | 10/1988 | Fischer | |
| 4,842,794 A | 6/1989 | Hovis | |
| 4,933,081 A | 6/1990 | Sasaki | |
| 5,077,870 A | 1/1992 | Melbye | |
| 5,260,015 A * | 11/1993 | Kennedy et al. | 264/167 |
| 5,290,377 A | 3/1994 | Aihara | |
| 5,300,058 A | 4/1994 | Goulait | |
| 5,419,695 A * | 5/1995 | Clegg | 425/296 |
| 5,605,735 A | 2/1997 | Zehner | |
| 5,660,778 A | 8/1997 | Ketcham | |
| 5,679,302 A | 10/1997 | Miller | |
| 5,692,271 A | 12/1997 | Provost | |
| 5,776,343 A | 7/1998 | Cullen et al. | |
| 5,845,375 A | 12/1998 | Miller | |
| 5,930,875 A | 8/1999 | Schreiner | |
| 5,945,131 A | 8/1999 | Harvey | |
| 5,953,797 A | 9/1999 | Provost | |
| 6,030,373 A | 2/2000 | VanGompel | |
| 6,039,911 A | 3/2000 | Miller | |
| 6,054,091 A | 4/2000 | Miller | |
| 6,132,660 A | 10/2000 | Kampfer | |
| 6,146,369 A | 11/2000 | Hartman | |
| 6,190,594 B1 | 2/2001 | Gorman | |
| 6,287,665 B1 | 9/2001 | Hammer | |
| 6,391,420 B1 | 5/2002 | Cederblad | |
| 6,489,003 B1 | 12/2002 | Levitt | |
| 6,575,953 B2 | 6/2003 | Olson | |
| 6,627,133 B1 | 9/2003 | Tuma | |
| 6,994,698 B2 | 2/2006 | Leak | |
| 7,001,475 B2 | 2/2006 | Ausen | |
| 7,032,278 B2 | 4/2006 | Kurtz, Jr. | |
| 7,048,818 B2 | 5/2006 | Krantz | |
| 7,125,400 B2 | 10/2006 | Igaue | |
| 7,198,743 B2 | 4/2007 | Tuma | |
| 7,214,334 B2 | 5/2007 | Jens et al. | |
| 7,241,483 B2 | 7/2007 | Ausen | |
| 7,371,302 B2 | 5/2008 | Miyamoto | |
| 7,373,698 B2 | 5/2008 | Erdman | |
| 7,407,496 B2 | 8/2008 | Petersen | |
| 7,670,522 B2 | 3/2010 | Ausen | |
| 7,897,078 B2 | 3/2011 | Petersen et al. | |
| 8,020,262 B2 | 9/2011 | Oertel | |
| 2002/0016581 A1 | 2/2002 | Kline | |
| 2002/0112325 A1* | 8/2002 | Keohan et al. | 24/452 |
| 2003/0008106 A1 | 1/2003 | Guenther | |
| 2003/0087059 A1 | 5/2003 | Jackson | |
| 2003/0130644 A1 | 7/2003 | Baker | |
| 2003/0229326 A1 | 12/2003 | Hovis | |
| 2004/0170801 A1* | 9/2004 | Seth et al. | 428/100 |
| 2004/0261232 A1 | 12/2004 | Kurtz, Jr. | |
| 2004/0261233 A1 | 12/2004 | Kingsford | |
| 2007/0039142 A1 | 2/2007 | Petersen | |
| 2007/0134489 A1 | 6/2007 | Neugebauer | |
| 2009/0217492 A1 | 9/2009 | Gallant | |
| 2011/0147475 A1 | 6/2011 | Biegler | |
| 2011/0151171 A1 | 6/2011 | Biegler | |
| 2011/0313389 A1 | 12/2011 | Wood | |
| 2012/0011685 A1 | 1/2012 | Rocha | |
| 2012/0204383 A1* | 8/2012 | Wood et al. | 24/306 |
| 2012/0330266 A1 | 12/2012 | Zonneveld | |

FOREIGN PATENT DOCUMENTS

| | | |
|---|---|---|
| EP | 1641417 | 4/2006 |
| GB | 2017485 | 10/1979 |
| GB | 2262906 | 7/1993 |
| JP | 2010-29532 | 2/2010 |
| WO | WO 94/20091 | 9/1994 |
| WO | WO 00/50229 | 8/2000 |
| WO | WO 2004/077980 | 9/2004 |
| WO | WO 2005/122818 | 12/2005 |
| WO | WO 2011/163193 | 12/2011 |
| WO | WO 2013/028654 | 2/2013 |
| WO | WO 2013/032683 | 3/2013 |
| WO | WO 2013/052371 | 4/2013 |

OTHER PUBLICATIONS

U.S. Application entitled, "Mechanical Closure Element", filed Aug. 16, 2012, having U.S. Appl. No. 29/429,801.
PCT/US2013/030143, filed Mar. 3, 2013.
International Search Report for PCT/US2013/054702, dated Oct. 25, 2013.

* cited by examiner

MECHANICAL FASTENING NETS AND METHODS OF MAKING THE SAME

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Hook and loop fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some hook members have been made with openings in the backing from which the hooks project. See, e.g., U.S. Pat. No. 4,001,366 (Brumlik) and U.S. Pat. No. 7,407,496 (Peterson), U.S. Pat. Appl. Pub. No. 2002/0112325 (Keohan et al.), and Int. Pat. Appl. Pub. Nos. WO 2005/122818 (Ausen et al.) and WO 1994/02091 (Hamilton).

SUMMARY

In one aspect, the present disclosure provides a method of making a mechanical fastening net. The method includes providing a net having strands of polymer and open areas between the strands of polymer, and molding a portion of the polymer in the strands of the net into upstanding posts to form the mechanical fastening net. It should be understood that the net and the upstanding posts are not formed simultaneously.

In another aspect, the present disclosure provides a mechanical fastening net. The mechanical fastening net has a polymeric backing with first and second major surfaces, a plurality of openings in the polymeric backing extending between the first and second major surfaces, and upstanding posts on at least one of the first or second major surface of the polymeric backing. The openings each have a series of areas through the openings from the first to second major surfaces ranging from minimum to maximum areas, and for at least a portion of the openings, the minimum area is not at either the first or second major surface.

In another aspect, the present disclosure provides a mechanical fastening net. The mechanical fastening net includes a polymeric backing having first and second major surfaces, a plurality of openings in the polymeric backing extending between the first and second major surfaces, and upstanding posts on at least one of the first or second major surface of the polymeric backing. Between the openings, the polymeric backing has a range of thicknesses ranging from minimum to maximum thickness, and for at least a portion of the polymeric backing, the minimum thickness of the polymeric backing is where it abuts one of the openings.

In the mechanical fastening nets of the foregoing aspects, the upstanding posts are generally molded from the polymer forming the polymeric backing.

In another aspect, the present disclosure provides a laminate comprising the mechanical fastening net according to and/or made according to any of the above aspects joined to a carrier.

The mechanical fastening nets according to and/or made according to any of the above aspects may be useful, for example, in laminates, strips, or patches that have a unique and attractive appearance. The openings can provide breathability and flexibility to the mechanical fastener, which may enhance the comfort of the wearer, for example, of an absorbent article comprising the mechanical fastener made by the method disclosed herein. The mechanical fastener also is typically able to cover a relatively larger area with a relatively smaller amount of material, which may lower its cost relative to a mechanical fastener not provided with openings. Also, because of the large area that may be covered by the mechanical fastener in an absorbent article, the mechanical fastener may provide performance enhancement, for example, by resist shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The mechanical fastener made according to the present disclosure may provide improved fit and closure stability by resisting such shifting because of its relatively larger area and flexibility. The amount of open area in the mechanical fastening net may be adjusted based upon, for example, the desired appearance, weight, or cost in the final product. The method disclosed herein allows openings to be provided in the mechanical fastener without wasteful material loss.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. In particular, in some embodiments certain components may be present in interchangeable and/or identical multiples (e.g., pairs). For these components, the designation of "first" and "second" may be applied to the components merely as a matter of convenience in the description of one or more of the embodiments.

The terms "multiple" and "a plurality" refer to more than one.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
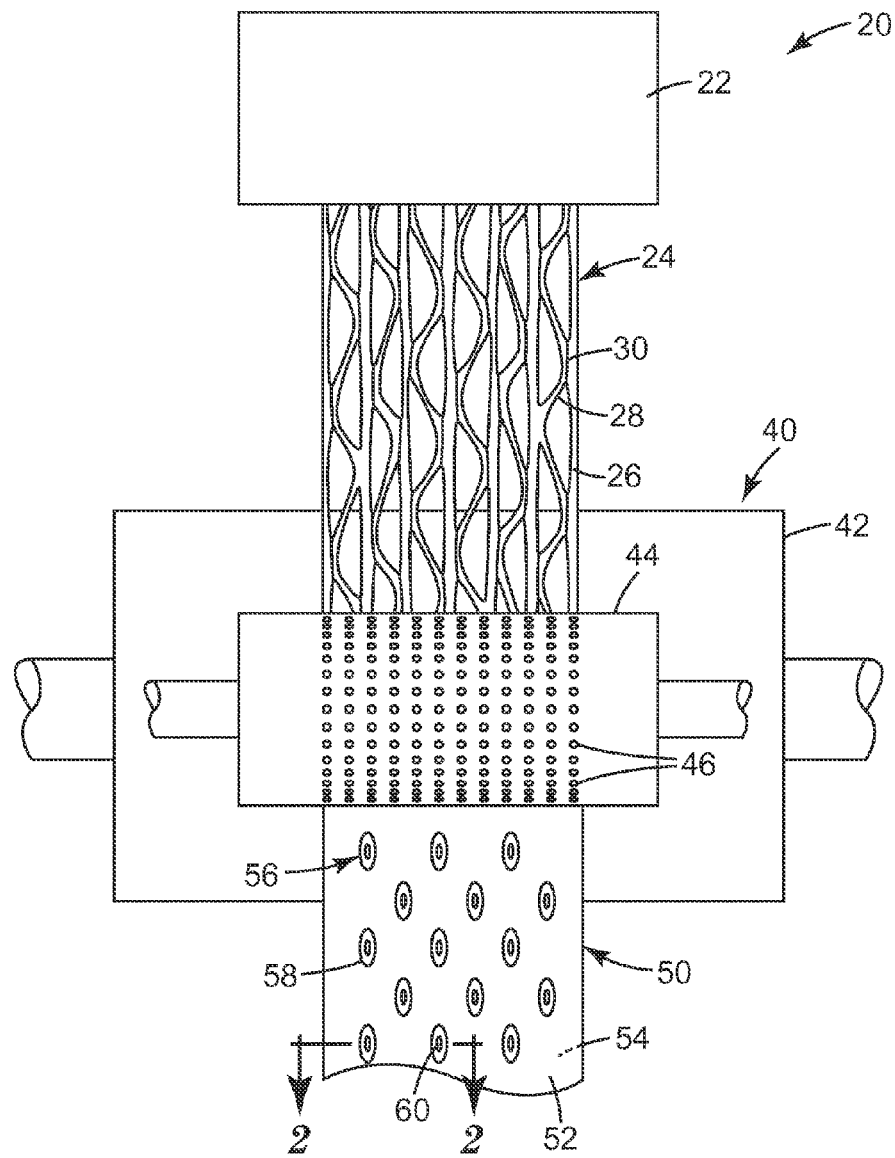
FIG. 1 is a schematic view of an embodiment of an apparatus useful for the method of making a mechanical fastening net according to the present disclosure.

FIG. 1 illustrates an embodiment of the method according to the present disclosure. In this embodiment, the method includes extruding the net. Referring to FIG. 1, exemplary apparatus 20 useful for carrying out the method disclosed herein is shown. Apparatus 20 has die 22 extruding a polymeric net 24 comprising first strands 26 and second strands 28. In the illustrated embodiment, first and second strands 26 and 28 are joined together at bond regions 30. As shown, polymeric netting 24 is extruded vertically, into nip 40. Vertical extrusion, that is, in the direction of gravity, may be useful, for example, for allowing collinear strands to collide with each other before becoming out of alignment with each other. Nip 40 includes backup roll 42, and a forming surface, which in the illustrated embodiment is forming roll 44. Forming roll 44 includes cavities 46 having the inverse shape of upstanding posts. In some embodiments, backup roll 42 is a smooth, chrome-plated steel roll and forming roll 44 is a silicone rubber roll. Forming roll 44 may also be a metal roll. In some embodiments, both backup roll 42 and forming roll 44 can be temperature controlled with, for example, internal water flow. In some embodiments, for example the one depicted here, polymeric net 24 passes directly into nip 40, and nip 40 is a quench nip. However, this is not considered necessary, and the extrusion of the netting and the entry into the nip need not be immediately sequential. After passing through nip 40, the polymeric net 24 has been transformed into a mechanical fastening net. In some embodiments, it may be advantageous to allow the mechanical fastening net to remain wrapped around forming roll 44 for at least a portion of its circumference.

Figure 2:
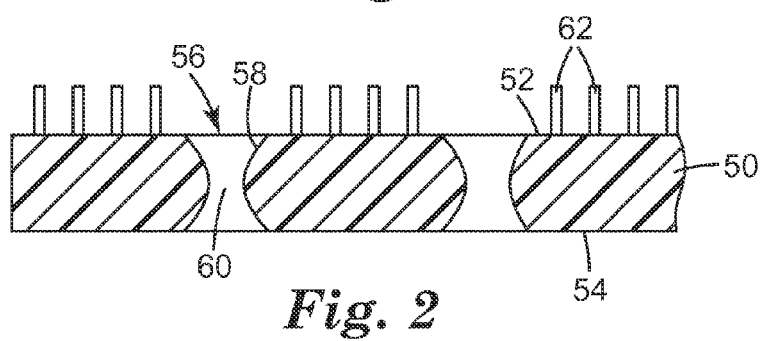
FIG. 2 is a cross-section view of an embodiment of the mechanical fastening net disclosed herein taken along section lines 2-2 in FIG. 1.

An embodiment of the mechanical fastening net according to the present disclosure is also shown in FIG. 1. Mechanical fastening net includes a polymer backing 50 with a first major surface 52 on the side towards the viewer, and second major surface 54 on the side opposite from the viewer. The first major surface 52 is provided with upstanding posts, which are not shown in FIG. 1 for visual clarity. Numerous openings 56 pass through polymeric backing 50 from first major surface 52 to second major surface 54. In the illustrated embodiment, openings 56 have well-formed, smooth edges 58. Further, in the illustrated embodiment, openings 56 taper inwards from both first major surface 52 and second major surface 54 so that opening 56 has a minimum area 60 somewhere in the interior of polymeric backing 50. These features of openings 56 can be better appreciated in FIG. 2, which is a cross-section view of polymeric backing 50 taken along section lines 2-2 in FIG. 1. The point where opening 56 tapers down to a minimum area 60 is shown to be in the interior of polymeric backing 50. It should be understood that the polymeric backing 50 is also at a minimum thickness at this point. Upstanding posts 62 on the polymer backing 50 are also shown in FIG. 2.

In embodiments, including the illustrated embodiment, wherein the openings each have a series of areas from the first to second major surfaces ranging from minimum to maximum areas, the position of the minimum area of the opening is typically influenced, for example, by the method of making the mechanical fastening net. For example, when an extruded, molten polymer net 24 is fed directly into nip 40, which is a quench nip, the outer surfaces of the first and second strands 26 and 28 tend to be cooled more quickly than the interior. This can typically occur after extruding a net without letting it completely solidify (in some embodiments, cool to room temperature). As a result, as the polymer net 24 is pressed in the nip, the interior of the strands tend to bulge outward more than the outer surfaces. In the resulting polymer backing 50 in the mechanical fastening net, for at least a portion of the openings 56, the minimum area 60 of the openings is not at either the first or second major surface 52 or 54. Further explanation and illustrations of this phenomenon can be found in co-pending application having U.S. Ser. No. 61/615, 676, filed Mar. 26, 2012, the disclosure of which is incorporated herein by reference. It has been observed that the temperature of the molten polymer, the temperature of the quench, and the thickness of the molten polymer affect the size of the openings. Higher melt temperature allows more movement of polymer in the nip which tends to create smaller opening sizes. Low temperature quenching has been shown to limit the amount of polymer movement which creates larger opening sizes.

In embodiments of the method according to the present disclosure that include extruding the net, a variety of methods of extruding a net may be useful. For example, the apparatus described in U.S. Pat. No. 4,038,008 (Larsen) may be useful.

In some embodiments, extruding the net includes providing an extrusion die having a plurality of shims positioned adjacent to one another, the shims together defining a first cavity and a second cavity, the extrusion die having a plurality of first dispensing orifices in fluid communication with the first cavity and having a plurality of second dispensing orifices connected to the second cavity, such that the first and second dispensing orifices are alternated. First polymeric strands are dispense from the first dispensing orifices at a first strand speed while simultaneously second polymeric strands are dispensed from the second dispensing orifices at a second strand speed, wherein the first strand speed is at least 2 times the second strand speed. In some embodiments, the first strand speed is in a range from 2 to 6 or from 2 to 4 times the second strand speed. In some embodiments, the first cavity of the extrusion die is supplied with a first polymer at a first pressure so as to dispense the first polymer from the first array at a first strand speed, the second cavity of the extrusion die is supplied with a second polymer at a second pressure so as to dispense the second polymer from the second array at a second strand speed, wherein the first strand speed is at least 2 (in some embodiments, 2 to 6, or 2 to 4) times the second strand speed. In some embodiments, the plurality of shims comprises a plurality of a repeating sequence of shims that includes a shim that provides a passageway between the first cavity and at least one of the first dispensing orifices and a shim that provides a passageway between the second cavity and the at least one of the second dispensing orifices.

Figure 3:
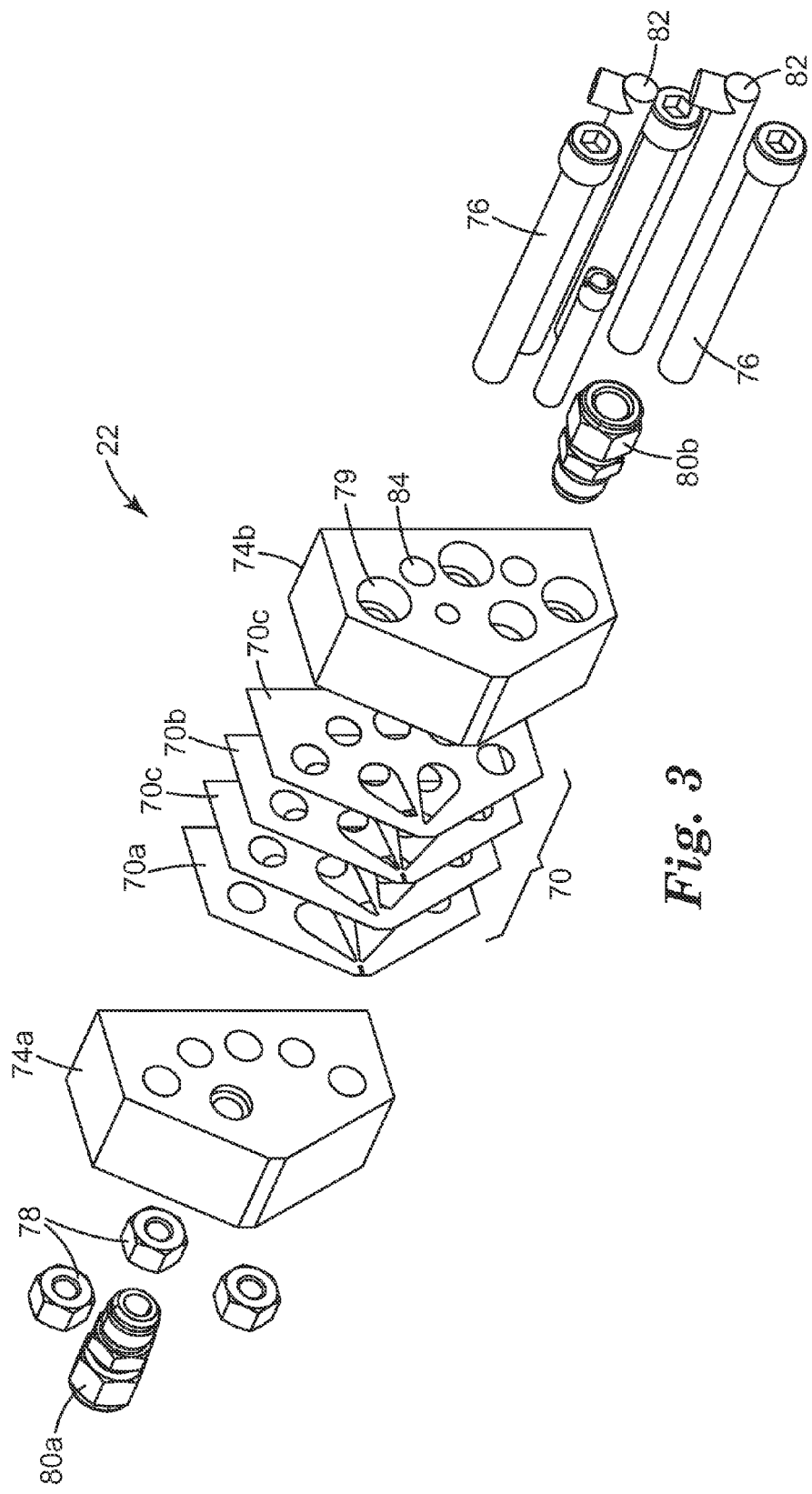
FIG. 3 is an exploded perspective view of an embodiment of a set of extrusion die elements suitable for use in the apparatus of FIG. 1, including a plurality of shims, a set of end blocks, bolts for assembling the components, and inlet fittings for the materials to be extruded.

For some of these embodiments, a useful extrusion die is illustrated in FIG. 3. In FIG. 3, extrusion die 22 includes plurality of shims 70. In some embodiments of extrusion dies described herein, there will be a large number of very thin shims 70 (typically several thousand shims; in some embodiments, at least 1000, 2000, 3000, 4000, 5000, 6000, 7000, 8000, 9000, or even at least 10,000), of diverse types (e.g., shims 70a, 70b, and 70c), compressed between two end blocks (e.g., 74a and 74b). Conveniently, fasteners (e.g., through bolts 76 threaded onto nuts 78) are used to assemble the components for extrusion die 22 by passing through holes 79. Inlet fittings 80a and 80b are provided on end blocks 74a and 74b respectively to introduce the materials to be extruded into extrusion die 22. In some embodiments, inlet fittings 80a and 80b are connected to melt trains of conventional type. In some embodiments, cartridge heaters 82 are inserted into receptacles 84 in extrusion die 22 to maintain the materials to be extruded at a desirable temperature while in the die. The ordinary artisan may perceive alternatives for assembling the extrusion die other than that shown in the illustrated embodiment. In some embodiments, the assembled shims (conveniently bolted between the end blocks) further comprise a manifold body (not shown) for supporting the shims. The manifold body has at least one (or more (e.g., two or three, four, or more)) manifold therein, the manifold having an outlet. An expansion seal (e.g., made of copper or alloys thereof) is disposed so as to seal the manifold body and the shims, such that the expansion seal defines a portion of at least one of the cavities (in some embodiments, a portion of both the first and second cavities), and such that the expansion seal allows a conduit between the manifold and the cavity.

Figure 4:
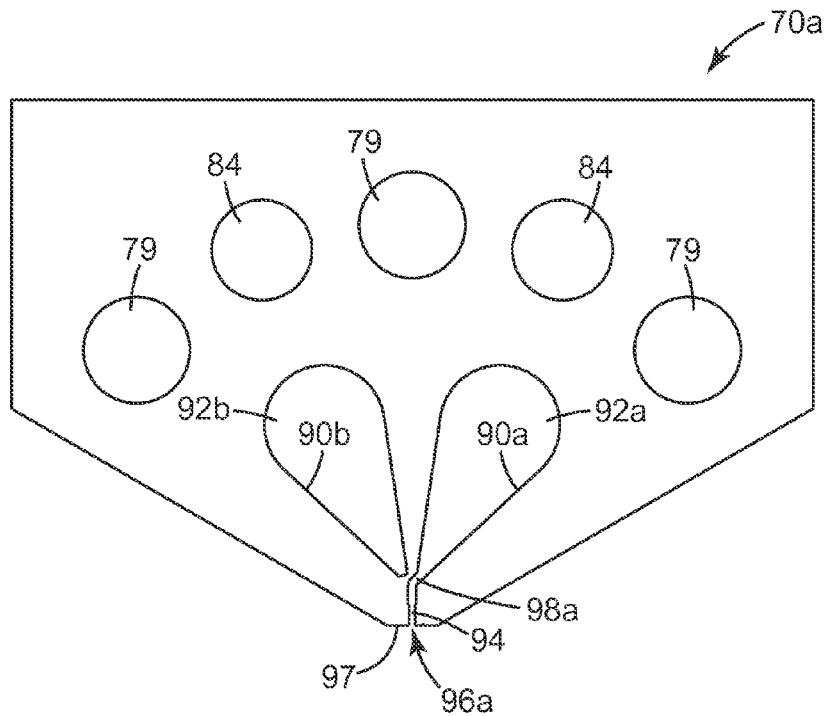
FIG. 4 is a plan view of one of the shims of FIG. 3.

Referring now to FIG. 4, a plan view of shim 70a from FIG. 3 is illustrated. Shim 70a has first aperture 90a and second aperture 90b. When extrusion die 22 is assembled, first apertures 90a in shims 70 together define at least a portion of first cavity 92a. Similarly, second apertures 90b in shims 70 together define at least a portion of second cavity 92b. Material to be extruded conveniently enters first cavity 92a via inlet port 80a, while material to be extruded conveniently enters second cavity 92b via inlet port 80b. Shim 70a has duct 94 ending in first dispensing orifice 96a in a dispensing surface 97. Shim 70a further has passageway 98a affording a conduit between first cavity 92a and duct 94. The dimensions of duct 94, and especially first dispensing orifice 96a at its end, are constrained by the dimensions desired in the polymer strands extruded from them. Since the strand speed of the strand emerging from first dispensing orifice 96a is also of significance, manipulation of the pressure in cavity 92a and the dimensions of passageway 98a can be used to set the desired strand speed.

Figure 5:
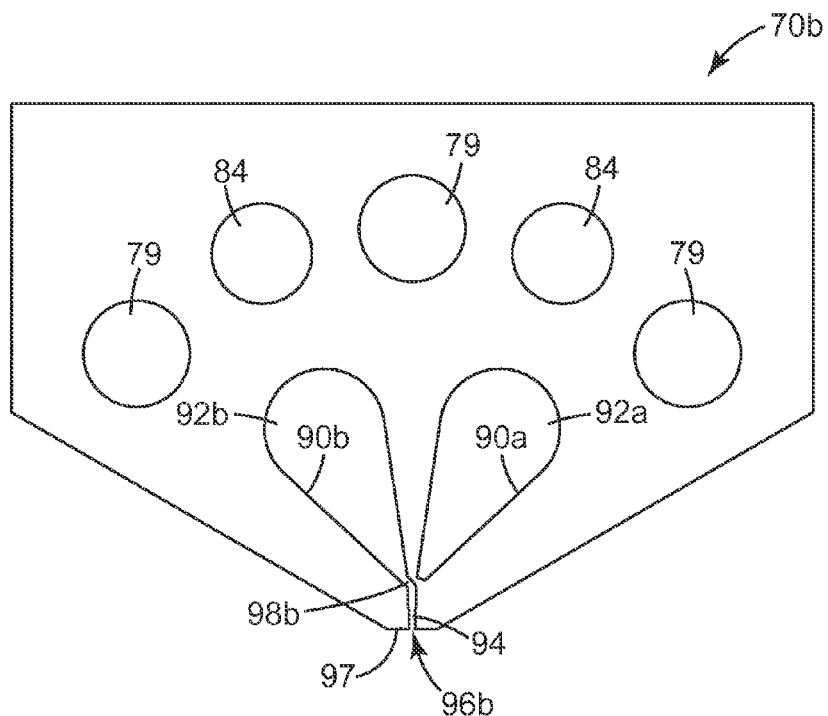
FIG. 5 is a plan view of another one of the shims of FIG. 3.

Referring now to FIG. 5, shim 70b is a reflection of shim 70a, having a passageway instead affording a conduit between second cavity 92b and second dispensing orifice 96b.

Figure 6:
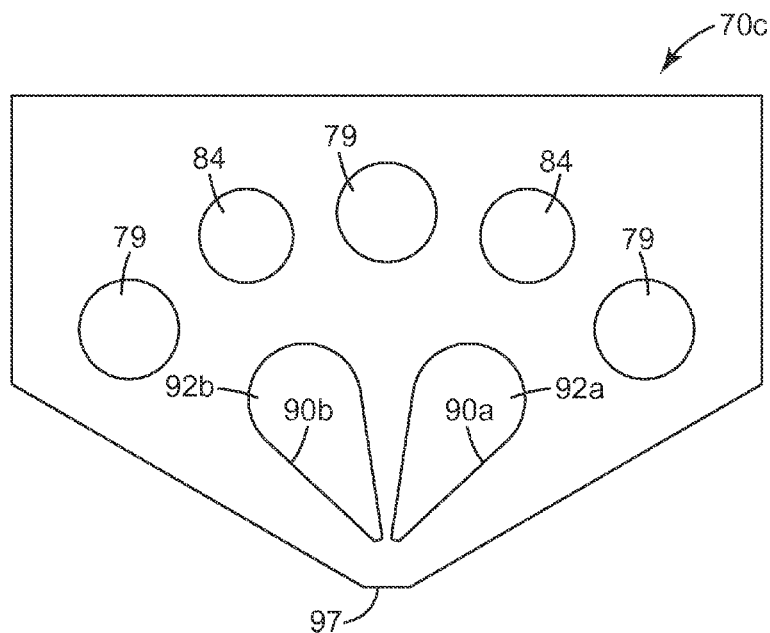
FIG. 6 is a plan view of yet another one of the shims of FIG. 3.

Referring now to FIG. 6, a plan view of shim 70c from FIG. 3 is illustrated Shim 70c has no passageway between either of first or second cavities 92a and 92b, respectively, and no duct opening onto dispensing surface 97.

The shims can have thicknesses in the range from 50 micrometers to 500 micrometers, although thicknesses outside of this range may also be useful. The shims are typically metal, for example, stainless steel. To reduce size changes with heat cycling, metal shims are typically heat-treated. The shims can be made by conventional techniques, including wire electrical discharge and laser machining. Often, a plurality of shims are made at the same time by stacking a plurality of sheets and then creating the desired openings simultaneously. Variability of the flow channels is preferably within 0.025 mm (1 mil), more preferably, within 0.013 mm (0.5 mil). The shims are tightly compressed to prevent gaps between the shims and polymer leakage. For example, 12 mm (0.5 inch) diameter bolts are typically used and tightened, at the extrusion temperature, to their recommended torque rating. Also, the shims are aligned to provide uniform extrusion out the extrusion orifice, as misalignment can lead to strands extruding at an angle out of the die which inhibits desired bonding of the net. To aid in alignment, an alignment key can be cut into the shims. Also, a vibrating table can be useful to provide a smooth surface alignment of the extrusion tip.

In some embodiments, the shims are assembled according to a plan that provides a repeating sequence of shims of diverse types, such as shims 70a, 70b, and 70c, illustrated in FIGS. 4, 5, and 6. The repeating sequence can have two or more shims per repeat. For example, a two-shim repeating sequence could comprise a shim that provides a passageway between the first cavity and a first dispensing orifice (e.g., shim 70a) and a shim that provides a passageway between the second cavity and a second dispensing orifice (e.g., shim 70b). In another example, a four-shim repeating sequence could comprise a shim that provides a passageway between the first cavity and a dispensing surface (e.g., shim 70a), a spacer shim (e.g., shim 70c), a shim that provides a passageway between the second cavity and a dispensing orifice (e.g., shim 70b), and a spacer shim (e.g., shim 70c).

When the shims are assembled, the cross-sectional shapes of the passageways may be, for example, square or rectangular. The shape of the passageways within, for example, a repeating sequence of shims, may be identical or different. For example, in some embodiments, the shims that provide a passageway between the first cavity and a first dispensing orifice might have a flow restriction compared to the shims that provide a conduit between the second cavity and a second dispensing orifice. The width of the distal opening within, for example, a repeating sequence of shims, may be identical or different. For example, the portion of the distal opening provided by the shims that provide a conduit between the first cavity and a first dispensing orifice could be narrower than the portion of the distal opening provided by the shims that provide a conduit between the second cavity and a second dispensing orifice. Furthermore, the shape of a dispensing orifice within, for example, a repeating sequence of shims, may be identical or different. For example, a 4-shim repeating sequence could be employed having a shim that provides a passageway between the first cavity and first dispensing orifice, a spacer shim, a shim that provides a passageway between the second cavity and a second dispensing orifice, and a spacer shim, wherein the shims that provide a passageway between the second cavity and a second dispensing orifice have a narrowed passage displaced from both edges of the distal opening, relative to the shims that provide a passageway between the first cavity and the first dispensing orifice. Also, each of the first and second dispensing orifices can have a different cross sectional area.

Typically, the first fluid passageways have greater fluid restriction than the second fluid passageways. Typically, the fluid passageways have thicknesses in a range from 50 micrometers to 750 micrometers, and lengths less than 5 mm (with generally a preference for smaller lengths for decreasingly smaller passageway thicknesses), although thicknesses and lengths outside of these ranges may also be useful. For large diameter fluid passageways several smaller thickness shims may be stacked together, or single shims of the desired passageway width may be used.

In some embodiments of the dies useful for extruding a polymer, each of the first and the second dispensing orifices have a width, and each of the first and the second dispensing orifices are separated by up to 2 times the width of the respective dispensing orifice. The spacing between orifices is sufficient to maintain a distance between adjacent strands as they exit the die. This spacing accommodates die swell at the dispensing tip. This spacing between orifices allows the strands after extrusion at different speeds to repeatedly collide with each other to form the repeating bonds of the net. If the spacing between orifices is too great the strands will not collide with each other and will not form the net.

In general, it has been observed that the rate of strand bonding is proportional to the extrusion speed of the faster strand. Further, it has been observed that this bonding rate can be increased, for example, by increasing the polymer flow rate for a given orifice size, or by decreasing the orifice area for a given polymer flow rate. It has also been observed that the distance between bonds is inversely proportional to the rate of strand bonding, and proportional to the speed that the net is drawn away from the die. Thus, it is believed that the distance between bonds and the net basis weight can be independently controlled by design of the orifice cross sectional area, the takeaway speed, and the extrusion rate of the polymer. For example, relatively high basis weight nettings, with a relatively short bond pitch can be made by extruding at a relatively high polymer flow rate, with a relatively low netting takeaway speed, using a die with a relatively small strand orifice area.

The size (same or different) of the strands can be adjusted, for example, by the composition of the extruded polymers, velocity of the extruded strands, and/or the orifice design (e.g., cross sectional area (e.g., height and/or width of the orifices)). For example, a first polymer orifice that is 3 times greater in area than the second polymer orifice can generate a net with equal strand sizes while meeting the velocity difference between adjacent strands.

Figure 7:
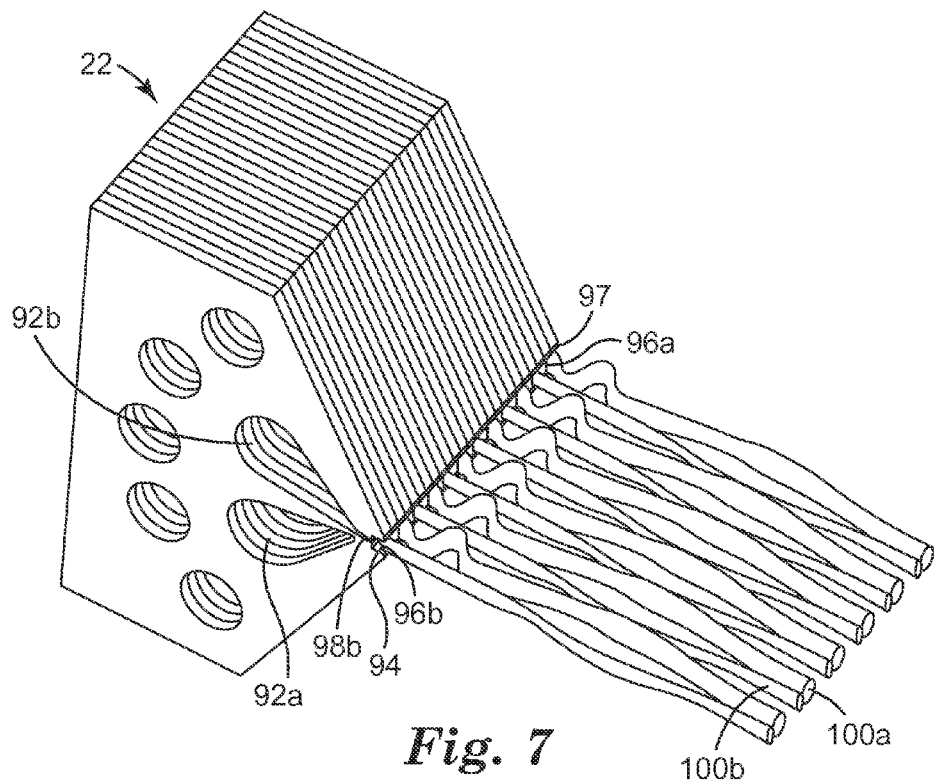
FIG. 7 is a schematic perspective view of a portion of the extrusion die of FIG. 3, supplied with polymeric material and forming a net.

Referring now to FIG. 7, a schematic perspective view of a portion of extrusion die 22 is illustrated, supplied with polymeric material and forming a net. Polymer from first cavity 92a emerges as first strands 100a from first dispensing orifices 96a, and second strands 100b are emerging from second dispensing orifices 96b. Passageways 98a (hidden behind the nearest shim in this view) and 98b, and the pressures in cavities 92a and 92b are typically selected so that the strand speed of first strands 100a are between about 2 and 6 (in some embodiments, 2 and 4) times greater than the strand speed of second strands 100b.

Although in the embodiment shown in FIG. 7, the first and second dispensing orifices are collinear, this is not a requirement. In some embodiments, the first dispensing orifices are collinear with each other, and the second dispensing orifices are collinear with each other, but the first and second dispensing orifices are not collinear. When the first and second dispensing orifices are not collinear with each other, it may be desirable to extrude the strands horizontally.

Figure 7A:
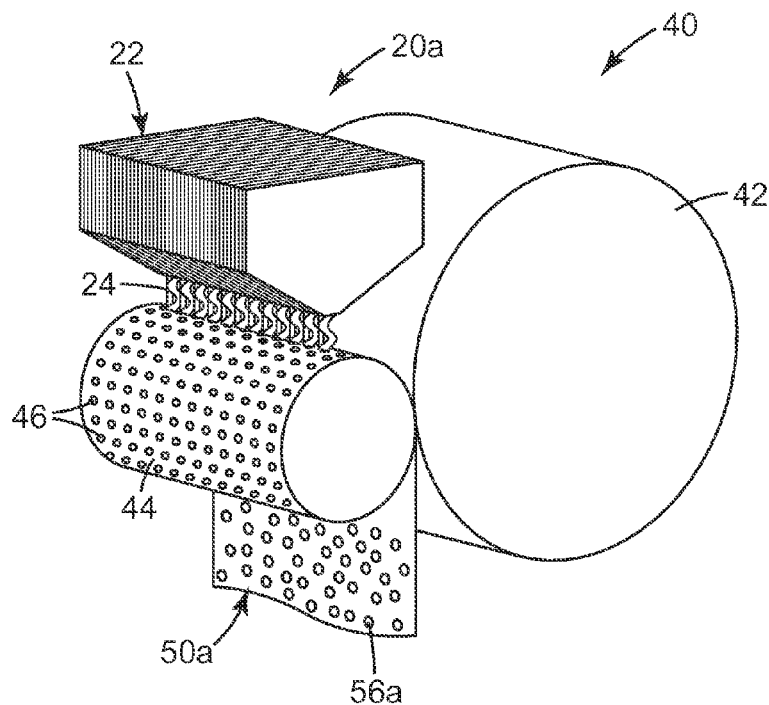
FIG. 7a is a schematic perspective view of another embodiment of an apparatus useful for the method of making a mechanical fastening net according to the present disclosure having a different arrangement of the extrusion die relative to the nip than the apparatus shown in FIG. 1.

Referring now to FIG. 7a, a schematic perspective view of another exemplary apparatus 20a with a different arrangement of extrusion die 22 relative to the nip 40 is shown. In alternate apparatus 20a, extrusion die 22 is positioned so that the polymeric netting 24 is dispensed onto forming roll 44 and carried on that roller into the nip between forming roll 44 and backup roller 42. By positioning extrusion die 22 quite close to forming roll 44, there is little time for the strands that make up polymeric netting 24 to sag and extend under the force of gravity. An advantage provided by this positioning is that openings 56a in polymer backing 50a tend to be rounder. More in this regard can be achieved by extruding not only very close to one of the rolls forming nip 40, but also at an extrusion speed similar to the circumferential speed of that roll. In FIG. 7a, again for visual clarity, upstanding posts on the polymer backing 50a are not shown along with openings 56a.

Figure 7B:
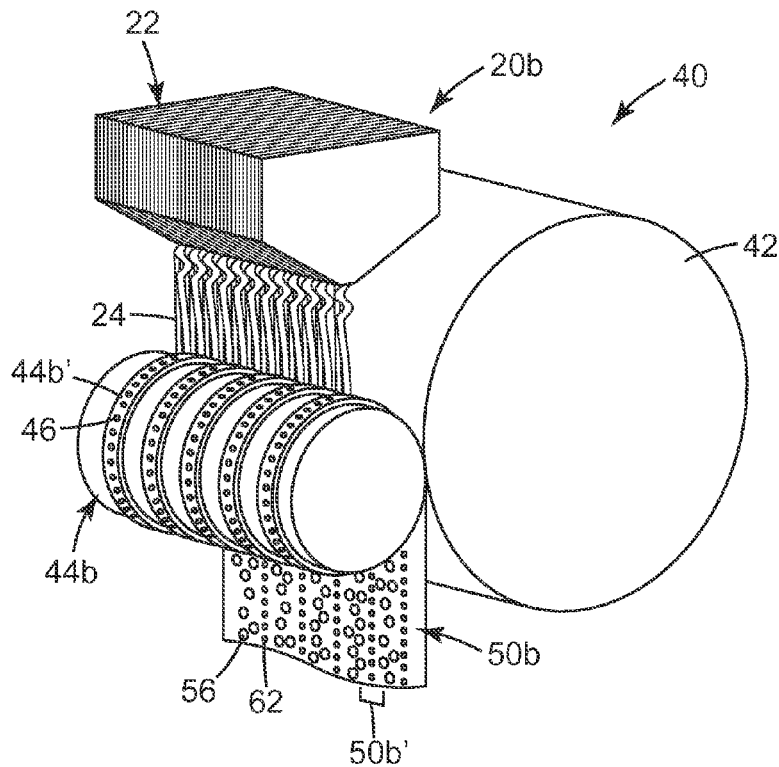
FIG. 7b is a schematic perspective view of an alternate nip roll.

Referring now to FIG. 7b, a schematic perspective view of another exemplary apparatus 20b with an alternate forming roll 44b is shown. The surface of alternate forming roll 44b includes raised areas 44b' with cavities 46 having the inverse shape of upstanding posts. Raised areas 44b' apply more nipping force on polymeric netting 24 against backup roll 42 than the other areas of nip forming roll 44b. In the depicted embodiment, enough force has been applied by raised areas 44b' that openings 56 in polymeric backing 50b are separated by longitudinal bands 50b' of solid layer where the potential openings have been crushed completely closed within nip 40 and where the forming roll 44b' provides bands 50b' with upstanding posts 62. Further, the relative thickness of the extruded polymeric netting has been found to affect the range of hole sizes; with a relatively thick netting it is easier to nip the melt to form longitudinal bands 50b' of solid film.

In the embodiments shown in FIGS. 1, 7a, and 7b and in some other embodiments of the method disclosed herein in which net extrudate is fed onto a continuously moving forming surface with cavities having the inverse shape of the upstanding posts, pressure provided by the nip forces the resin into the cavities. In some embodiments, a vacuum can be used to evacuate the cavities for easier filling of the cavities. The forming surface and cavities can optionally be air or water cooled before stripping the mechanical fastening net having upstanding posts from the forming surface such as by a stripper roll.

Suitable technologies for making cavities in a roll include employing a series of plates defining a plurality of post-forming cavities about its periphery such as those described, for example, in U.S. Pat. No. 4,775,310 (Fischer). Cavities may be formed in the plates by drilling or photoresist technology, for example. Other suitable rolls with cavities may include wire-wrapped rolls, which are disclosed along with their method of manufacturing, for example, in U.S. Pat. No. 6,190,594 (Gorman et al.). Yet other suitable tool rolls are described in U.S. Pat. No. 6,287,665 (Hammer), U.S. Pat. No. 7,198,743 (Tuma), and U.S. Pat. No. 6,627,133 (Tuma). Another suitable forming surface includes using a flexible mold belt defining an array of upstanding post-shaped cavities as described in U.S. Pat. No. 7,214,334 (Jens et al.). For non-continuous processes, cavities can be drilled into plates (e.g., laser-drilled into silicone plates) used in a film press, for example.

In some embodiments, it may be desirable to pattern the second major surface of the polymeric backing. This can be achieved, for example, by patterning the surface of backup roller 42 shown in FIGS. 1, 7a, and 7b. Cavities in the backup roller 42 can provide upstanding posts on both the second major surface while the forming roll 44 or 44b provides upstanding posts on the first major surface of the polymeric backing. However, in some embodiments, the upstanding posts are on only the first major surface of the polymeric backing. This may be useful, for example, when joining the second major surface to a carrier as described in further detail below. The use of a textured roller, for example, for the backup roller 42, or providing nip roller 44 with additional surface texture, may be useful to preferentially move polymer in the cross direction or downweb direction. This can be useful for shaping the openings on one or both sides of the polymeric backing. Also, in some embodiments, it may be desired to quench one side of the film at a faster rate than the other, in order to affect the shape of the opening's cross-section.

While the embodiment of the method described above in connection with FIGS. 3 to 7 supply first and second strands of a polymer net from separate first and second cavities, other embodiments include providing an extrusion die comprising a plurality of shims positioned adjacent to one another, the shims together defining a cavity, the extrusion die having a plurality of first dispensing orifices in fluid communication with the cavity and a plurality of second dispensing orifices in fluid communication with the cavity, such that the first and second dispensing orifices are alternated. In these embodiments, first polymeric strands are dispensed from the first dispensing orifices at a first strand speed while simultaneously second polymeric strands are dispensed from the second dispensing orifices at a second strand speed, wherein the first strand speed is at least 2 times the second strand speed. In some embodiments, the cavity of the extrusion die is supplied with a first polymer at a first pressure so as to dispense a first strand at a first strand speed through a first passageway, and to dispense a second strand at a second strand speed through a second passageway, wherein the first strand speed is at least 2 (in some embodiments, 2 to 6, or even 2 to 4) times the second strand speed, such that a polymer net comprising first and second polymeric strands is formed.

Figure 11:
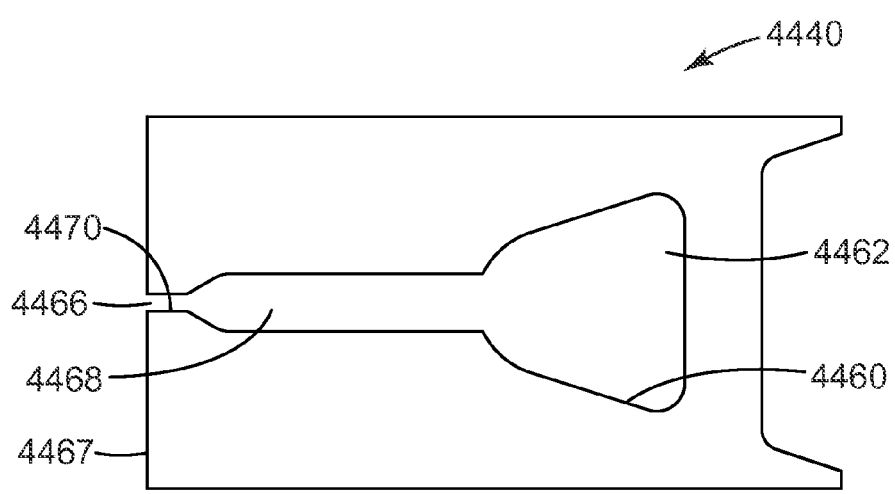
FIG. 11 is a plan view of an example of a shim for making netting extruded from a single cavity useful for some embodiments of the method of making a mechanical fastening net according to the present disclosure.

Referring now to FIG. 11, a plan view of shim 4440, useful in connection with a die for forming netting with first and second strands made from the same material and extruded from a single cavity, is illustrated. Shim 4440 has aperture 4460. When assembled with the shims of FIGS. 12 and 13 in the way described below in FIGS. 14 and 15, aperture 4460 will define at least a portion of cavity 4462. In use, passageway 4468 conducts polymer from cavity 4462 to first dispensing orifice 4466 on dispensing surface 4467. Importantly, there is restriction 4470 adjacent to first dispensing orifice 4466. Restriction 4470 increases the first strand speed of the first strand emerging from first dispensing orifice 4466 during use.

Figure 12:
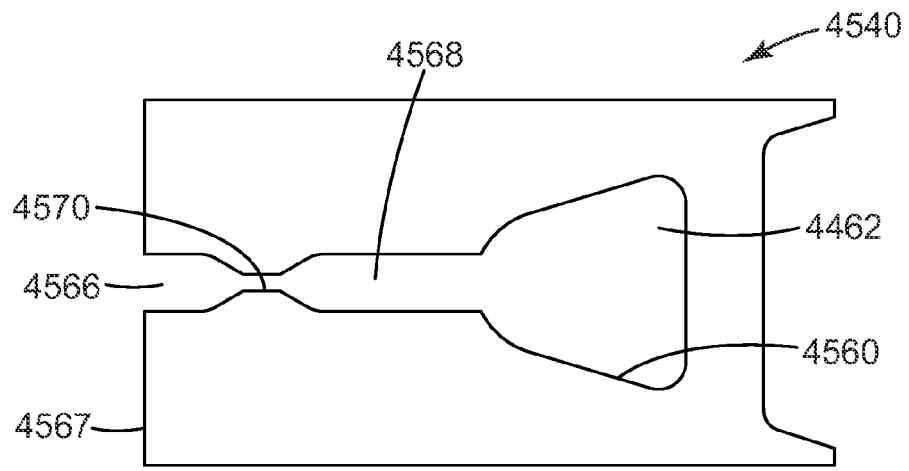
FIG. 12 is a plan view of an example of a shim for making netting useful in conjunction with the shim of FIG. 11.

Referring now to FIG. 12, a plan view of shim 4540 is illustrated. Shim 4540 has an aperture 4560. When assembled with the shims of FIGS. 11 and 13 in the way described below in FIGS. 14 and 15, aperture 4560 will define at least a portion of cavity 4462. In use, passageway 4568 conducts polymer from cavity 4462 to second dispensing orifice 4566 on dispensing surface 4567. There is restriction 4570 set back from second dispensing orifice 4566. The wide orifice 4566 decreases the speed of the second strand emerging from second dispensing orifice 4566 during use.

Figure 13:
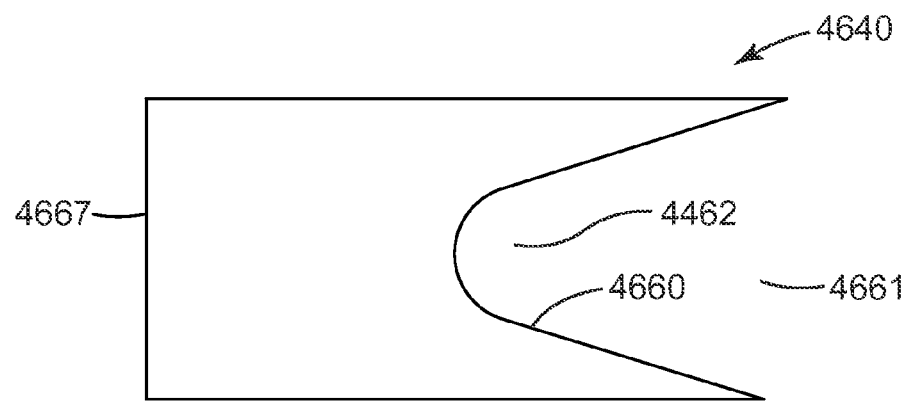
FIG. 13 is a plan view of an example of a spacer shim for making netting useful in conjunction with the shims of FIG. 11 and FIG. 12.

Referring now to FIG. 13, a plan view of spacer shim 4640 useful in forming netting in conjunction with the shims 4440 and 4540 of FIGS. 11 and 12, is illustrated Shim 4640 has cut-out 4660. When assembled with the shims of FIGS. 11 and 12 in the way described below in FIGS. 14 and 15, cut-out 4660 will define at least a portion of cavity 4462. Cut-out 4660 has open end 4661 on the end opposite dispensing surface 4667. Open end 4661 allows the inflow of polymer into cavity 4462 when assembled with the other shims and mounted in a die mount analogous to that shown above in FIG. 3.

Figure 14:
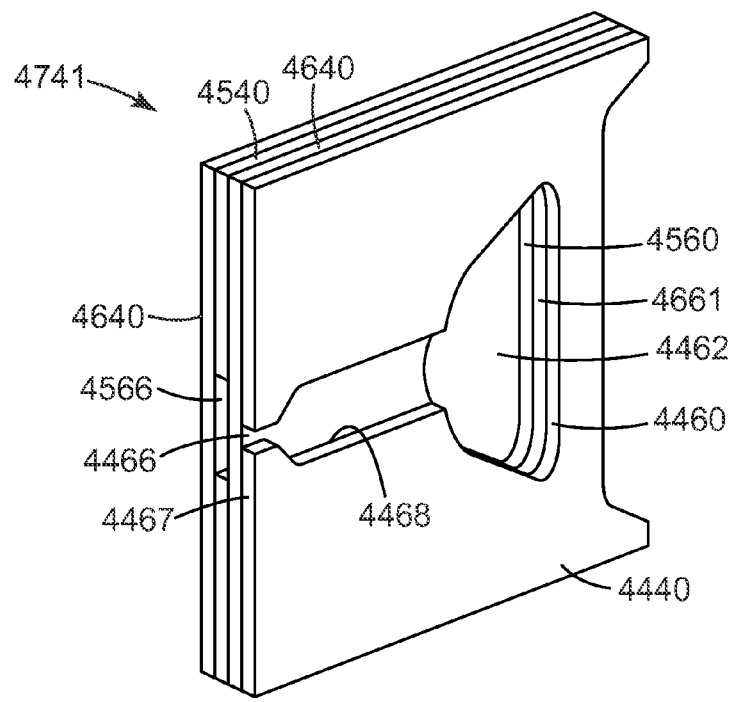
FIG. 14 is a detail perspective view of a plurality of shims formed from the shims of FIGS. 11, 12, and 13.

Referring now to FIG. 14, a detail perspective view of plurality of shims 4741 formed, from left to right, one spacer shim 4640, one shim 4540, one spacer shim 4640, and one shim 4440, is illustrated. In this view it can be appreciated how apertures 4460 and 4560, and cut-out 4660 (not labeled) together define a portion of cavity 4462. It will be apparent to the skilled artisan that for any particular extrusion pressure applied to cavity 4462 during extrusion, the mass flow of the first strand emerging from first dispensing orifice 4466 will be approximately equal to the mass flow of the second strand emerging from second dispensing orifice 4566. However, the first strand speed of the first strand will be significantly faster than the second strand speed of the second strand.

Figure 15:
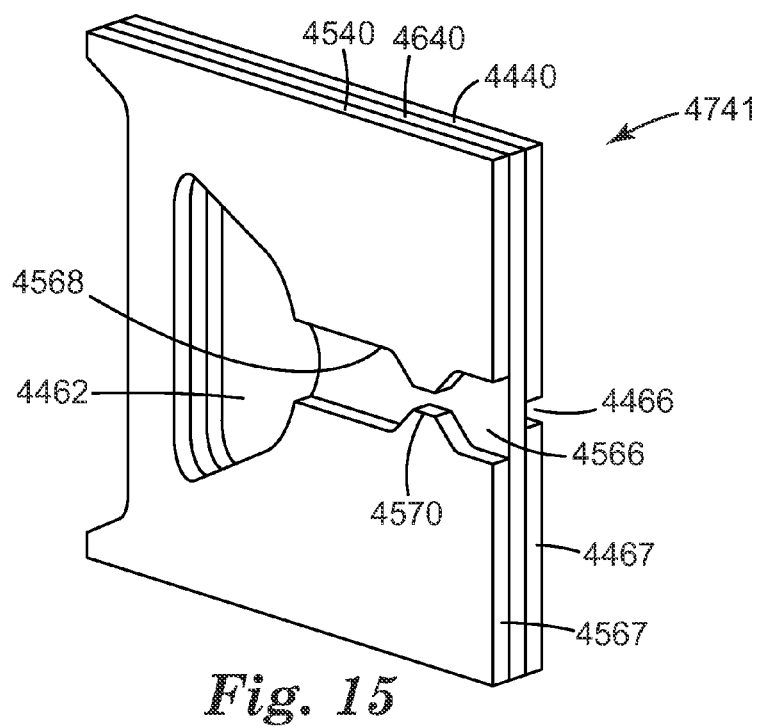
FIG. 15 is a detail perspective view of the plurality of shims of FIG. 14, seen from the reverse angle, with one of the shims removed from visual clarity.

Referring now to FIG. 15, a detail perspective view of the plurality of shims of FIG. 14, seen from the reverse angle, with the nearest instance of shim 4640 removed for visual clarity, is illustrated. In this view of the reduced plurality of shims 4741', restriction 4570 can be better appreciated.

Further details about the formation of nets from extrusion dies having one or more cavities can be found in co-pending application having U.S. Ser. No. 61/526,001, filed Aug. 22, 2011, the disclosure of which is incorporated herein by reference.

Examples of polymeric materials from which the mechanical fastening net can be made include thermoplastic polymers. Suitable thermoplastic polymers for mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In some embodiments, polymeric materials from which the mechanical fastening net can be made comprise a colorant (e.g., pigment and/or dye) for functional (e.g., optical effects) and/or aesthetic purposes (e.g., each has different color/shade). Suitable colorants are those known in the art for use in various polymeric materials. Exemplary colors imparted by the colorant include white, black, red, pink, orange, yellow, green, aqua, purple, and blue. In some embodiments, it is desirable level to have a certain degree of opacity for one or more of the polymeric materials. The amount of colorant(s) to be used in specific embodiments can be readily determined by those skilled in the (e.g., to achieve desired color, tone, opacity, transmissivity, etc.).

In some embodiments, nets comprising strands of polymer useful for the method described herein include alternating first and second polymeric strands, wherein the first and second polymeric strands comprise different polymeric compositions. These nets can be prepared, for example, by extrusion using any embodiments of the method described above in which the extrusion die includes first and second cavities. The different polymeric compositions in the first and second strands may be selected for their surface properties or their bulk properties (e.g., tensile strength, elasticity, color, etc). Furthermore, polymeric compositions can be selected to provide specific functional or aesthetic properties in the mechanical fastening net such as elasticity, softness, hardness, stiffness, bendability, or colors. The first and second polymer strands may have the same or different colors.

In some embodiments, a single strand of the strands of polymer in the net may include different polymeric compositions. For example, one or more of the strands in the net may have a core made of one polymeric composition and a sheath of a different polymeric composition. Such nets can be extruded as described in co-pending application having U.S. Ser. No. 61/530,521, filed Sep. 2, 2011, the disclosure of which is incorporated herein by reference. A portion of the polymer in these nets can be molded into upstanding posts immediately after extrusion while still molten as described above but this is not a requirement.

In embodiments in which the strands of polymer in the net useful for making a mechanical fastening net described herein include two different polymeric compositions, the first polymeric composition may be a thermoplastic polymer as described above, and the second polymeric composition may be a more elastic composition. For example, the second polymeric composition may include thermoplastic elastomers such as ABA block copolymers, polyurethane elastomers, polyolefin elastomers (e.g., metallocene polyolefin elastomers), polyamide elastomers, ethylene vinyl acetate elastomers, and polyester elastomers. An ABA block copolymer elastomer generally is one where the A blocks are polystyrenic, and the B blocks are conjugated dienes (e.g., lower alkylene dienes). In embodiments described above in which at least some of the polymer strands in the net are core/sheath strands, it may useful for the core to comprise a relative more elastic composition.

In any embodiments of the method described above in which a net is extruded, polymers used to make the polymeric strands are selected to be compatible with each other such that the first and second strands bond together as the bond regions. Bonding generally refers to melt-bonding, and the bonds between polymer strands can be considered to be melt-bonded. The bonding occurs in a relatively short period of time (typically less than 1 second). The bond regions, as well as the strands, typically cool through air and natural convection and/or radiation. In selecting polymers for the strands, in some embodiments, it may be desirable to select polymers of bonding strands that have dipole interactions (or H-bonds) or covalent bonds. Bonding between strands has been observed to be improved by increasing the time that the strands are molten to enable more interaction between polymers. Bonding of polymers has generally been observed to be improved by reducing the molecular weight of at least one polymer and or introducing an additional co-monomer to improve polymer interaction and/or reduce the rate or amount of crystallization. In some embodiments, the distance between bonds is in a range from 0.5 mm to 20 mm (in some embodiments, in a range from 0.5 mm to 10 mm).

In any embodiments of the method described above in which a net is extruded, the strands of polymer typically do not substantially cross over each other (i.e., at least 50 (at least 55, 60, 65, 70, 75, 80, 85, 90, 95, 99, or even 100) percent by number do not cross over each other).

According to some embodiments of the method disclosed herein, mechanical fastening nets can be made by at least one of passing through a nip or calendering any net comprising strands of polymer and open areas between the strands of polymer, whether made by the above-described extrusion methods or not. Such nets can be made from any of the polymers described above in connection with extrusion methods for making a net.

When the polymeric strands of the net, including any net whether prepared according to the extrusion methods described above or not, are solid instead of molten, molding the upstanding posts can include pressing the net onto a heated mold surface with cavities having the inverse shape of the upstanding posts. This mold surface may be moving as described above or stationary. In these embodiments, the polymeric backing in the resulting mechanical fastening net tends to have a range of thicknesses, and the polymer backing tends to be thinnest where it abuts an opening. Also, in many of these embodiments, the openings have irregularly formed perimeters. This can mean that the openings have irregular shapes (that is, no lines of symmetry). They may have edges that are not smooth (e.g., jagged or feathery edges). Irregularly formed openings can also have a variety of thicknesses of the backing surrounding the openings. These features can depend, for example, on the temperature and length of time used during the molding as well as on the selection polymeric material in the net.

In some embodiments, the strands of polymer in the net useful for the method of making the mechanical fastening net disclosed herein have an average width in a range from 10 micrometers to 500 micrometers (in a range from 10 micrometers to 400 micrometers, or even 10 micrometers to 250 micrometers).

In some embodiments, the net comprising strands of polymer useful for the method of making the mechanical fastening net disclosed herein have a basis weight in a range from 5 $g/m^2$ to 400 $g/m^2$ (in some embodiments, 10 $g/m^2$ to 200 $g/m^2$).

In some embodiments, the net comprising strands of polymer useful in the method of making the mechanical fastening net disclosed herein has a thickness up to 2 mm (in some embodiments, up to 1 mm, 500 micrometers, 250 micrometers, 100 micrometers, 75 micrometers, 50 micrometers, or even up to 25 micrometers; in a range from 10 micrometers to 750 micrometers, 10 micrometers to 750 micrometers, 10 micrometers to 500 micrometers, 10 micrometers to 250 micrometers, 10 micrometers to 100 micrometers, 10 micrometers to 75 micrometers, 10 micrometers to 50 micrometers, or even 10 micrometers to 25 micrometers. In some embodiments, the net comprising strands of polymer has an average thickness in a range from 250 micrometers to 5 mm. In some embodiments, the net comprising strands of polymer has an average thickness not greater than 5 mm.

The upstanding posts molded in the strands of the net in any of the methods and mechanical fastening nets described herein may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element with a loop-engaging head may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts. Furthermore, portions cut from such ribs are noticeable different from the molded posts described herein as would be seen by a person having ordinary skill in the art. For example, molded posts do not typically have flat sides such as those that are formed by cutting.

If the posts formed upon exiting the cavities do not have loop-engaging heads, loop-engaging heads could be subsequently formed by a capping method as described in U.S. Pat. No. 5,077,870 (Melbye et al.). Typically, the capping method includes deforming the tip portions of the upstanding posts using heat and/or pressure. The heat and pressure, if both are used, could be applied sequentially or simultaneously. The method of making a mechanical fastening net disclosed herein can also include a step in which the shape of the cap is changed, for example, as described in U.S. Pat. No. 6,132,660 (Kampfer).

In some embodiments of the mechanical fastening net or the method of making a mechanical fastening net disclosed herein, each upstanding post has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the polymer backing). In other embodiments, the upstanding posts may have the shape of a J (e.g., as shown in U.S. Pat. No. 5,953,797 (Provost et al.).

In some embodiments of the mechanical fastening net according to and/or made according to the present disclosure, the upstanding posts have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

Figure 9:
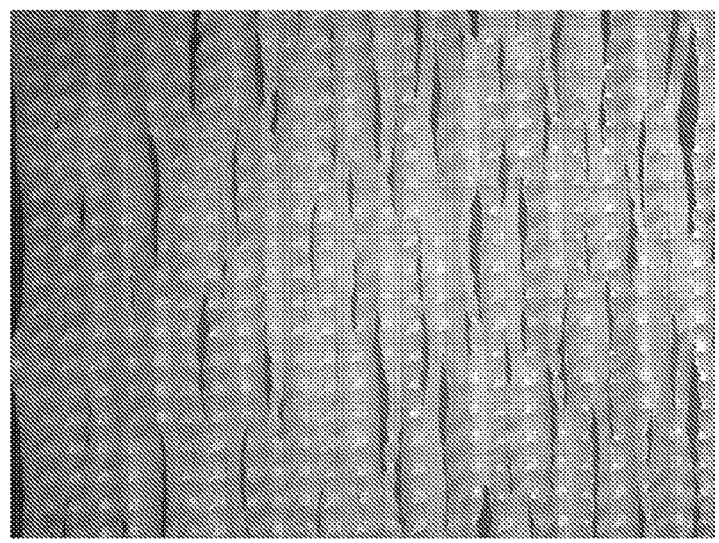
FIG. 9 is an optical digital photo of the mechanical fastening net of Example 1.
Figure 17:
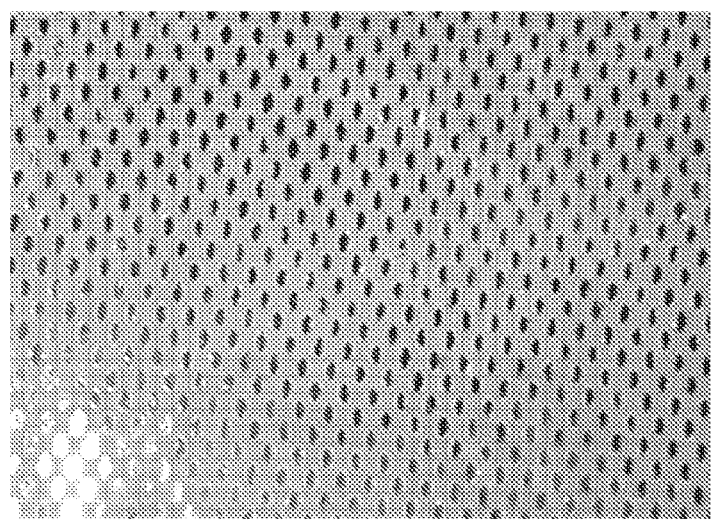
FIG. 17 is an optical digital photo showing a top view of the mechanical fastening net of Example 2.

In some embodiments of the mechanical fastening net according to and/or made according to the present disclosure, in at least some locations of the polymeric backing between the openings, there is a plurality of the upstanding posts. In some of these embodiments, the plurality of the upstanding posts is provided in multiple rows of upstanding posts, each row having at least two upstanding posts. This can be seen, for example, in many locations in the mechanical fastening nets shown in FIGS. 9 and 17. While FIGS. 9 and 17 illustrate the upstanding posts are formed in rows, in other embodiments, the upstanding posts may be formed in a random pattern.

In some embodiments of the mechanical fastening net according to and/or made according to the present disclosure, in at least some locations of the polymeric backing between the openings, the locations are larger in each dimension than at least the bases of the upstanding posts. This can also be seen, for example, in many locations in the mechanical fastening nets shown in FIGS. 9 and 17.

In some embodiments of the mechanical fastening net according to and/or made according to the present disclosure, the strands from the net are still visible after a portion of the strands are molded into upstanding posts. This can be seen, for example, in FIG. 9. In other embodiments, the strands from the net are no longer visible after a portion of the strands are molded into upstanding posts. This can be seen, for example, in FIG. 17.

In some embodiments, mechanical fastening nets according to and/or made according to the present disclosure have a backing thickness (not including the upstanding posts) up to 200 micrometers (in some embodiments, up to 150 micrometers, 100 micrometers, 75 micrometers, or 50 micrometers; in a range from 10 micrometers to 200 micrometers, 10 micrometers to 150 micrometers, 10 micrometers to 100 micrometers, 30 micrometers to 200 micrometers, 30 micrometers to 150 micrometers, 30 micrometers to 100 micrometers, or 30 micrometers to 75 micrometers.

In some embodiments, mechanical fastening nets described herein have a total open area for each of the first and second, generally opposed major surfaces of not greater than 50 (in some embodiments, not greater than 45, 40, 35, 30, 25, 20. 15, 10, 5, 4 3, 2, 1, 0.75, 0.5, 0.25, or even not greater than 0.1) percent of the total area of the respective major surface.

In some embodiments, for at least a majority of the openings of the mechanical fastening nets described herein, the maximum area of each opening is not greater than is 5 (in some embodiments, not greater than 2.5, 2, 1, 0.5, 0.1, 0.05, 0.01, 0.075, or even not greater than 0.005)mm$^2$. Individual openings range from 0.005 mm$^2$ to 5 mm$^2$ In some embodiments, the openings have widths in a range from 5 micrometers to 1 mm (in some embodiments, 10 micrometers to 0.5 mm) In some embodiments, the openings have lengths in a range from 100 micrometers to 10 mm (in some embodiments, 100 micrometers to 1 mm) In some embodiments, for mechanical fastening nets described herein the openings have a length to width ratio in a range from 1:1 to 100:1, (in some embodiments, 1:1 to 1.9:1, 2:1 to 100:1 2:1 to 75:1, 2:1 to 50:1, 2:1 to 25:1, or even, 2:1 to 10:1).

In some embodiments, mechanical fastening nets according to the present disclosure have in a range from 50,000 to 6,000,000 (in some embodiments, 100,000 to 6,000,000, 500, 000 to, 6,000,000, or even 1,000,000 to 6,000,000) openings/m$^2$.

In some embodiments, the openings of the mechanical fastening nets described herein have at least two pointed ends. In some embodiments, at least some of the openings are elongated with two pointed ends. In some embodiments, at least some of the openings are elongated with two opposed pointed ends. In some embodiments, at least some of the openings are ovals.

In some embodiments of the mechanical fastening net or the method of making the mechanical fastening net according to the present disclosure, the mechanical fastening net may be stretched in at least one direction. In a continuous process (e.g., after the mechanical fastening net exits from the nip) monoaxial stretching in the machine direction can be performed by propelling the web over rolls of increasing speed. Means such as diverging rails and diverging disks are useful for cross-direction stretching. A versatile stretching method that allows for monoaxial, sequential biaxial, or simultaneous biaxial stretching of a thermoplastic web employs a flat film tenter apparatus. Such an apparatus grasps the thermoplastic web using a plurality of clips, grippers, or other film edge-grasping means along opposing edges of the thermoplastic web in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany. The term "machine direction" (MD) as used above and below denotes the direction of a running, continuous web of the net during the manufacturing of the mechanical fastening net. The term "cross-direction" (CD) as used above and below denotes the direction which is essentially perpendicular to the machine direction.

In some embodiments, the mechanical fastening net according to and/or made according to the present disclosure is joined to a carrier (e.g., even a sacrificial carrier) for ease of handling or for making a fastening laminate for a selected application. The mechanical fastening net may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier may be continuous (i.e., without any through-penetrating holes) or discontinuous (e.g. comprising through-penetrating perforations or pores). The carrier may comprise a variety of suitable materials including woven webs, nonwoven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof In some embodiments, the carrier is a fibrous material (e.g., a woven, nonwoven, or knit material). Examples of materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In some embodiments where the mechanical fastening net includes a thermoplastic backing, the thermoplastic backing can be joined to a fibrous web carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto. In some of these embodiments, the joining comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the fibrous layer, loop, or upstanding posts the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

In some embodiments wherein the mechanical fastening net is joined to a carrier, one or more zones of the carrier may comprise one or more elastically extensible materials extending in at least one direction when a force is applied and returning to approximately their original dimension after the force is removed. However, in some embodiments, at least the portion of the carrier joined to the multiple strands of the backing or loop material is not stretchable. In some embodiments, the portion of carrier joined to the multiple strands will have up to a 10 (in some embodiments, up to 9, 8, 7, 6, or 5) percent elongation in the CD. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC). In some embodiments, the carrier is not pleated. The term "elastic" refers to any material that exhibits recovery from stretching or deformation. "Elongation" in terms of percent refers to {(the extended length–the initial length)/the initial length} multiplied by 100.

In some embodiments wherein the mechanical fastening net is joined to a carrier, the carrier is provided with a layer of adhesive. In some of these embodiments, the mechanical fastening net is bonded to the carrier with the adhesive to form a laminate, and the adhesive is exposed at least some of the openings.

In some embodiments, the method according to the present disclosure includes cutting a running length of the mechanical fastening net in the CD to provide a mechanical fastening patch. Such cutting can be carried out, for example, after the mechanical fastening net is laminated to a carrier, and the patch can be considered a fastening laminate.

The fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the spread mechanical fastening patch thereby providing a fingerlift. When the spread mechanical fastening patch is used in a fastening tab, exposed adhesive that may be present in some embodiments in at least some of the openings of the mechanical fastening patch may be useful for "anti-flagging" or for maintaining the disposable absorbent article in a rolled up state after use. Also when the mechanical fastening patch is used as a fastening tab, exposed adhesive that may be present in some embodiments between the multiple strands of the spread mechanical fastening patch may be useful to provide a combination of mechanical and adhesive fastening. The fastening laminate made by the methods disclosed herein may also be useful, for example, for disposable articles such as sanitary napkins.

The mechanical fasteners and laminates made according to the present disclosure may also be useful in many other fastening applications, for example, assembly of automotive parts or any other application in which releasable attachment may be desirable.

Some Embodiments of the Disclosure

In a first embodiment, the present disclosure provides a method of making a mechanical fastening net, the method comprising:

providing a net comprising strands of polymer and open areas between the strands of polymer; and molding a portion of the polymer in the strands of the net into upstanding posts to form the mechanical fastening net.

In a second embodiment, the present disclosure provides the method of the first embodiment, wherein the strands are periodically bonded together at bond regions throughout the net.

In a third embodiment, the present disclosure provides the method of the first or second embodiment, wherein the strands do not cross each other.

In a fourth embodiment, the present disclosure provides the method of any one of the first to third embodiments, wherein the strands of polymer are solid.

In a fifth embodiment, the present disclosure provides the method of the fourth embodiment, wherein molding comprises pressing the net onto a heated mold surface with cavities having the inverse shape of the upstanding posts.

In a sixth embodiment, the present disclosure provides the method of the fourth or fifth embodiment, wherein the mechanical fastening net comprises a polymeric backing comprising first and second major surfaces, a plurality of openings in the polymeric backing extending between the first and second major surfaces, and upstanding posts on at least one of the first or second major surface of the polymeric backing, wherein between the openings, the polymeric backing has a range of thicknesses ranging from minimum to maximum thickness, wherein for at least a portion of the polymeric backing, the minimum thickness of the polymeric backing is where it abuts one of the openings.

In a seventh embodiment, the present disclosure provides the method of the sixth embodiment, wherein the openings have irregularly formed perimeters.

In an eighth embodiment, the present disclosure provides the method of any one of the first to third embodiments, wherein the strands of polymer are molten.

In a ninth embodiment, the present disclosure provides the method of the eighth embodiment, wherein providing the net comprises extruding the net.

In a tenth embodiment, the present disclosure provides the method of the ninth embodiment, wherein extruding the net comprises:

providing an extrusion die comprising a plurality of shims positioned adjacent to one another, the shims together defining a cavity, the extrusion die having a plurality of first dispensing orifices in fluid communication with the cavity and a plurality of second dispensing orifices in fluid communication with the cavity, such that the first and second dispensing orifices are alternated; and dispensing first polymeric strands from the first dispensing orifices at a first strand speed while simultaneously dispensing second polymeric strands from the second dispensing orifices at a second strand speed, wherein the first strand speed is at least 2 times the second strand speed to provide the net.

In an eleventh embodiment, the present disclosure provides the method of the ninth embodiment, wherein extruding the net comprises:

providing an extrusion die comprising a plurality of shims positioned adjacent to one another, the shims together defining a first cavity and a second cavity, the extrusion die having a plurality of first dispensing orifices in fluid communication with the first cavity and having a plurality of second dispensing orifices connected to the second cavity, such that the first and second dispensing orifices are alternated; and dispensing first polymeric strands from the first dispensing orifices at a first strand speed while simultaneously dispensing second polymeric strands from the second dispensing orifices at a second strand speed, wherein the first strand speed is at least 2 times the second strand speed to provide the net.

In a twelfth embodiment, the present disclosure provides the method of any one of the eighth to eleventh embodiments, wherein molding a portion of the polymer in the strands of the net into upstanding posts comprises:

providing a net extrudate upon extruding the net; and feeding the net extrudate onto a continuously moving forming surface with cavities having the inverse shape of the upstanding posts.

In a thirteenth embodiment, the present disclosure provides the method of the twelfth embodiment, wherein the continuously moving forming surface is a first roll that forms a nip with a second roll.

In a fourteenth embodiment, the present disclosure provides the method of any one of the eighth to thirteenth embodiments, wherein the mechanical fastening net comprises a polymeric backing comprising first and second major surfaces, a plurality of openings in the polymeric backing extending between the first and second major surfaces, and upstanding posts on at least one of the first or second major surface of the polymeric backing, wherein between the openings, the polymeric backing has a range of thicknesses ranging from minimum to maximum thickness, wherein for at least a portion of the polymeric backing, the minimum thickness of the polymeric backing is where it abuts one of the openings.

In a fifteenth embodiment, the present disclosure provides the method of any one of the eighth to thirteenth embodiments, wherein the mechanical fastening net comprises a polymeric backing comprising first and second major surfaces, a plurality of openings in the polymeric backing extending between the first and second major surfaces, and upstanding posts on at least one of the first or second major surface of the polymeric backing, wherein the openings each have a series of areas through the openings from the first to second major surfaces ranging from minimum to maximum areas, and wherein for at least a portion of the openings, the minimum area is not at either the first or second major surface.

In a sixteenth embodiment, the present disclosure provides the method of any one of the first to fifteenth embodiments, further comprising deforming at least some of the upstanding posts at their distal ends to form loop-engaging overhangs.

In a seventeenth embodiment, the present disclosure provides a mechanical fastening net comprising a polymeric backing comprising first and second major surfaces, a plurality of openings in the polymeric backing extending between the first and second major surfaces, and upstanding posts on at least one of the first or second major surface of the polymeric backing, wherein between the openings, the polymeric backing has a range of thicknesses ranging from minimum to maximum thickness, wherein for at least a portion of the polymeric backing, the minimum thickness of the polymeric backing is where it abuts one of the openings.

In an eighteenth embodiment, the present disclosure provides the mechanical fastening net of the seventeenth embodiment, wherein the openings each have a series of areas through the openings from the first to second major surfaces ranging from minimum to maximum areas, and wherein for at least a portion of the openings, the minimum area is not at either the first or second major surface.

In a nineteenth embodiment, the present disclosure provides the mechanical fastening net of the seventeenth embodiment, the openings have irregularly formed perimeters.

In a twentieth embodiment, the present disclosure provides a mechanical fastening net comprising a polymeric backing comprising first and second major surfaces, a plurality of openings in the polymeric backing extending between the first and second major surfaces, and upstanding posts on at least one of the first or second major surface of the polymeric backing, wherein the openings each have a series of areas through the openings from the first to second major surfaces ranging from minimum to maximum areas, and wherein for at least a portion of the openings, the minimum area is not at either the first or second major surface.

In a twenty-first embodiment, the present disclosure provides the mechanical fastening net of any one of the seventeenth to twentieth embodiments, wherein the upstanding posts are on only the first major surface of the polymeric backing.

In a twenty-second embodiment, the present disclosure provides the mechanical fastening net of any one of the seventeenth to twenty-first embodiments, wherein in at least some locations of the polymeric backing between the openings, there is a plurality of the upstanding posts.

In a twenty-third embodiment, the present disclosure provides the mechanical fastening net of any one of the seventeenth to twenty-second embodiments, wherein the plurality of the upstanding posts is provided in multiple rows of upstanding posts, each row having at least two upstanding posts.

In a twenty-fourth embodiment, the present disclosure provides the mechanical fastening net of any one of the seventeenth to twenty-third embodiments, wherein for at least some locations of the polymeric backing between the openings, the locations have a length and a width perpendicular to the thickness of the net, and wherein the length and width are both larger than at least the bases of the upstanding posts.

In a twenty-fifth embodiment, the present disclosure provides the mechanical fastening net of any one of the seventeenth to twenty-fourth embodiments, wherein there is a total area and a total open area for each of the first and second major surfaces, and wherein the total open area for each of the first and second major surfaces is not greater than 50 percent of the total area of the respective major surface.

In a twenty-sixth embodiment, the present disclosure provides the mechanical fastening net of any one of the seventeenth to twenty-fifth embodiments, having a thickness of up to 200 micrometers.

In a twenty-seventh embodiment, the present disclosure provides a laminate comprising the mechanical fastening net of any one of the seventeenth to twenty-sixth embodiments joined to a carrier.

In a twenty-eighth embodiment, the present disclosure provides the laminate of the twenty-seventh embodiment, wherein the mechanical fastening net is joined to the carrier with adhesive.

In a twenty-ninth embodiment, the present disclosure provides the laminate of the twenty-eighth embodiment, wherein the adhesive is exposed in at least some of the openings.

In a thirtieth embodiment, the present disclosure provides the method of any one of the first to sixth embodiments, wherein the strands of polymer are not all the same color.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

EXAMPLES

Example 1

Figure 8:
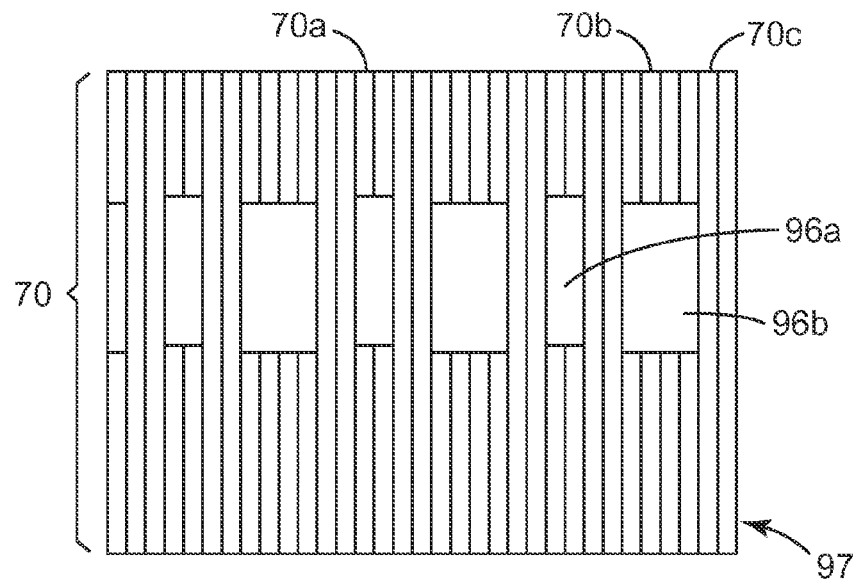
FIG. 8 is a close up front view of the dispensing surface of an extrusion die used in certain of the Examples.

A co-extrusion die as generally depicted in FIG. 3, and assembled with a 10 shim repeating pattern of extrusion orifices as generally illustrated in FIG. 7, was prepared. The thickness of the shims in the repeat sequence was 4 mils (102 mm) for shims 70 with connection to the first cavity, the second cavity, and for the spacers which had no connection to either cavity (70a, 70b and 70c, respectively). The shims were formed from stainless steel, with perforations cut by a wire electron discharge machining. The height of first and second extrusion orifices 96a and 96b was cut to 30 mils (0.762 mm). The extrusion orifices were aligned in a collinear, alternating arrangement, and resulting dispensing surface 97 was as shown generally in FIG. 8. Two spacer shims followed by two shims with connection to the first cavity, followed by two spacer shims, followed by 4 shims with connection to the second cavity comprises the shim stack sequence. The total width of the shim setup was 15 cm. The orifice width for first extrusion orifices 96a leading to the first cavity was 0.204 mm, and the orifice width for second extrusion orifices 96b leading to the second cavity was 0.408 mm. The land spacing between the first and second orifices was 0.204 mm.

The inlet fittings on the two end blocks were each connected to a conventional single-screw extruder. The extruder feeding the first cavity was loaded with thirty-five melt flow index polypropylene copolymer pellets (obtained under the trade designation "C700-35N" from Dow Chemical Company, Midland, Mich.). The extruder feeding the second cavity was also loaded with thirty-five melt flow index polypropylene copolymer pellets ("C700-35N") and a 2% loading of blue pigment masterbatch.

The net was extruded vertically into an extrusion quench takeaway nip. The quench nip had a metal surface provided with 1600 cavities per square inch and was set to a temperature of 150° C. The nip pressure was sufficient to fill the cavities to a height of 0.350 mm. Polymers were extruded from the two cavities at appropriate flow rates to make a net, and the quench take away speed was 13.0 meters per minute. A schematic of the process is shown in FIG. 1.

Using an optical microscope, the backing thickness and upstanding post height of the mechanical fastening net were measured. The backing thickness ranged from 0.060 mm to 0.070 mm, and the height of the posts was 0.0350 mm. The general shape of the openings was vesica piscis.

Figure 10:
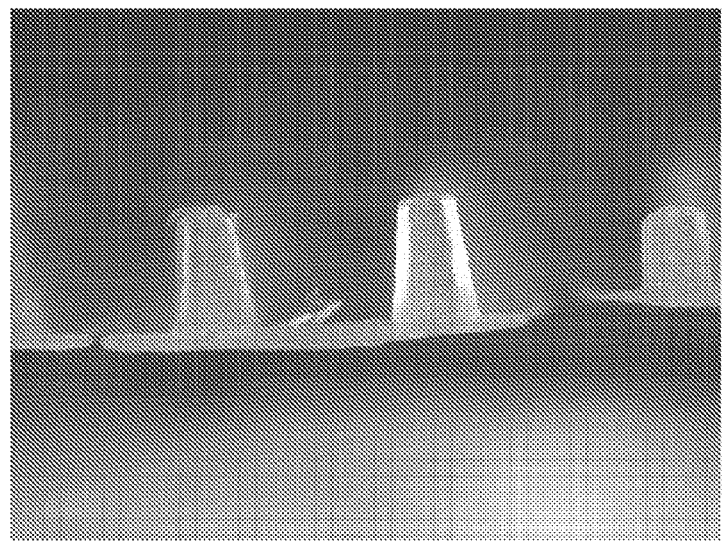
FIG. 10 is a scanning electron digital photomicrograph of the cross-section of one of the holes of the mechanical fastening net shown in FIG. 9.

An optical digital photo at 10× of the mechanical fastening net is shown in FIG. 9. An optical digital photo taken from the side at 150× is shown in FIG. 10. It can be seen in the side view that the backing thickness is at a minimum where it abuts an opening. It can also been seen in the side view that minimum area of the openings are in the interior of the backing and not at either the first or second major surface.

The upstanding posts could be capped using a variety of capping methods.

Example 2

Figure 16:
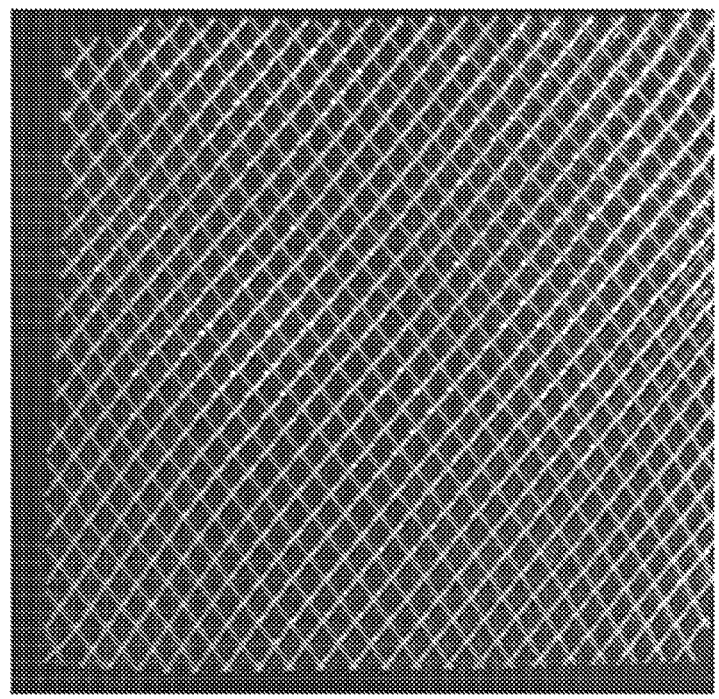
FIG. 16 is an optical digital photo of the polymeric net starting material for Example 2.
Figure 18:
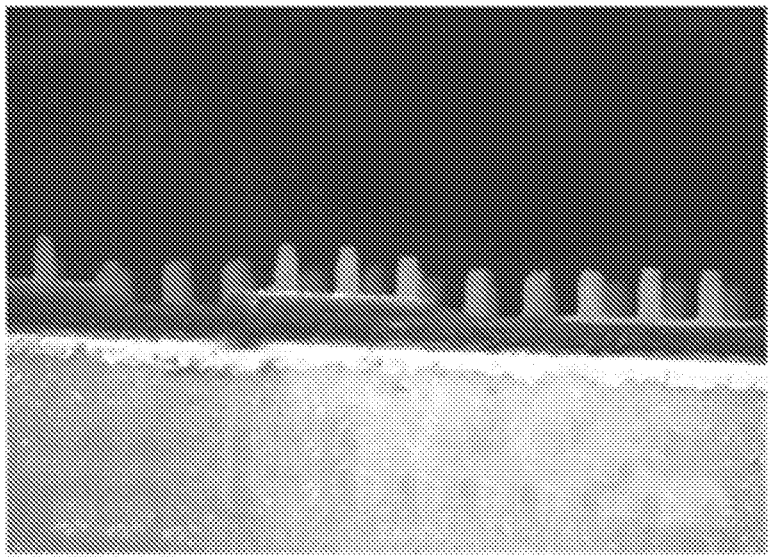
FIG. 18 is an optical digital photo showing a cross-sectional view of the mechanical fastening net of Example 2.
Figure 19:
FIG. 19 is an optical digital photo showing a top view of the mechanical fastening net of Example 2 at higher magnification than in FIG. 17.

Polypropylene netting (style NFNC 605-002) was obtained from Conwed, (Minneapolis, Minn.). A photo of the polypropylene netting is shown in FIG. 16. A film press obtained from (Wabash MPI, Wabash, Ind.), was used to form upstanding posts in the polypropylene netting. The platens of the film press were preheated to 350° F. (177° C.). A sandwich was then made by assembling a smooth steel plate approximately 0.125 inch (3.2 mm) thick, a 20-mil (0.51-mm) thick silicone plate with laser-drilled holes to produce posts, the polypropylene netting, 1 sheet of 4 mil (0.1 mm) polyethylene terephthalate (PET) film, and a second smooth steel plate approximately 0.125 inch (3.2 mm) thick. The holes had diameters of a nominal 325 micrometers. The sandwich was placed between the platens at low pressure to warm up the sandwich plates. Then the 6-inch (15 cm) by 6-inch (15 cm) sample was pressed at approximately 10 tons (the pressure was 3.8 megapascals) to press the polymer into the silicone plate. The sample was cooled with a cold platen. A photograph of the pressed sample is shown in FIG. 17. An optical digital photo at 100× of a side view of the pressed sample shown in FIG. 18. An optical digital photo at 200× of the pressed sample shown in FIG. 19, where thick and thin areas of the backing are apparent. Using an optical microscope, the dimensions of the pressed sample were measured. The posts were measured to be 700 micrometers high, and the polymer backing was measured to be 90 micrometers thick.

Then the posts were capped using a household iron with wax paper. The iron was set to "wool". The wax paper was set on top of the stems to be capped. The iron was set on top of the wax paper and posts for approximately 5 seconds.

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. A mechanical fastening net comprising:
a polymeric backing comprising first and second major surfaces, a plurality of openings in the polymeric backing extending between the first and second major surfaces, and upstanding posts on at least one of the first or second major surface of the polymeric backing, wherein for a portion of the polymeric backing between two adjacent openings not having upstanding posts abutting the two adjacent openings, the polymeric backing has a minimum thickness where it abuts one of the two adjacent openings that is smaller than a maximum thickness of the polymeric backing at a location between the two adjacent openings.

2. The mechanical fastening net of claim 1, wherein the upstanding posts are on only the first major surface of the polymeric backing 3. The mechanical fastening net of claim 1, wherein in at least some locations of the polymeric backing between the openings, there is a plurality of the upstanding posts.

4. The mechanical fastening net of claim 1, wherein for at least some locations of the polymeric backing between the openings, the locations have a length and a width perpendicular to the thickness of the net, and wherein the length and width are both larger than at least the bases of the upstanding posts.

5. A laminate comprising the mechanical fastening net of claim 1 joined to a carrier.

6. The laminate of claim 5, wherein the mechanical fastening net is joined to the carrier with adhesive, and wherein the adhesive is exposed in at least some of the openings.

7. A method of making the mechanical fastening net of claim 1, the method comprising:
providing a net comprising strands of polymer and open areas between the strands of polymer; and molding a portion of the polymer in the strands of the net into upstanding posts to form the mechanical fastening net.

8. The method of claim 7, wherein the strands are periodically bonded together at bond regions throughout the net, and wherein the strands do not cross each other.

9. The method of claim 7, wherein the strands of polymer are solid.

10. The method of claim 9, wherein molding comprises pressing the net onto a heated mold surface with cavities having the inverse shape of the upstanding posts.

11. The method of claim 7, wherein the strands of polymer are molten.

12. A mechanical fastening net comprising:
   a polymeric backing comprising first and second major surfaces, a plurality of openings in the polymeric backing extending between the first and second major surfaces, and upstanding posts on at least one of the first or second major surface of the polymeric backing,
   wherein for at least some of the openings, each opening has a series of different areas through the opening in a number of planes parallel to the first to second major surfaces ranging from a smaller, minimum area to a larger, maximum area, and wherein the smaller, minimum area is not at either the plane of the first major surface or the plane of the second major surface.

13. The mechanical fastening net of claim 12, wherein in at least some locations of the polymeric backing between the openings, there is a plurality of the upstanding posts.

14. The mechanical fastening net of claim 12, wherein for at least some locations of the polymeric backing between the openings, the locations have a length and a width perpendicular to the thickness of the net, and wherein the length and width are both larger than at least the bases of the upstanding posts.

15. A laminate comprising the mechanical fastening net of claim 12 joined to a carrier, wherein the mechanical fastening net is joined to the carrier with adhesive, and wherein the adhesive is exposed in at least some of the openings.

16. A method of making the mechanical fastening net of claim 12, the method comprising:
   extruding a net comprising strands of polymer and open areas between the strands of polymer; and
   molding a portion of the polymer in the strands of the net into upstanding posts to form the mechanical fastening net.

17. The method of claim 16, wherein extruding the net comprises:
   providing an extrusion die comprising a plurality of shims positioned adjacent to one another, the shims together defining a cavity, the extrusion die having a plurality of first dispensing orifices in fluid communication with the cavity and a plurality of second dispensing orifices in fluid communication with the cavity, such that the first and second dispensing orifices are alternated; and
   dispensing first polymeric strands from the first dispensing orifices at a first strand speed while simultaneously dispensing second polymeric strands from the second dispensing orifices at a second strand speed, wherein the first strand speed is at least 2 times the second strand speed to provide the net.

18. The method of claim 16, wherein extruding the net comprises:
   providing an extrusion die comprising a plurality of shims positioned adjacent to one another, the shims together defining a first cavity and a second cavity, the extrusion die having a plurality of first dispensing orifices in fluid communication with the first cavity and having a plurality of second dispensing orifices connected to the second cavity, such that the first and second dispensing orifices are alternated; and
   dispensing first polymeric strands from the first dispensing orifices at a first strand speed while simultaneously dispensing second polymeric strands from the second dispensing orifices at a second strand speed, wherein the first strand speed is at least 2 times the second strand speed to provide the net.

19. The method of claim 16, wherein molding a portion of the polymer in the strands of the net into upstanding posts comprises:
   providing a net extrudate upon extruding the net; and
   feeding the net extrudate onto a continuously moving forming surface with cavities having the inverse shape of the upstanding posts.

20. The method of claim 19, wherein the continuously moving forming surface is a first roll that forms a nip with a second roll.

* * * * *